United States Patent [19]

Jaunakais et al.

[11] Patent Number: 5,106,581
[45] Date of Patent: Apr. 21, 1992

[54] TEST DEVICE FOR DETECTION OF MOLYBDATE, VANADATE AND FERRIC IONS

[75] Inventors: Ivars Jaunakais, Rock Hill, S.C.; James K. Jaunakais, Phoenix, Ariz.

[73] Assignee: Industrial Test Systems, Inc., Rock Hill, S.C.

[21] Appl. No.: 707,793

[22] Filed: May 30, 1991

[51] Int. Cl.$^5$ .......... G01N 31/22; G01N 33/20/21/77
[52] U.S. Cl. ....................... 422/56; 422/58; 436/83; 436/84; 436/169
[58] Field of Search ............. 422/56, 58; 436/83, 436/84, 169

[56] References Cited

U.S. PATENT DOCUMENTS

| | | | |
|---|---|---|---|
| 3,252,761 | 5/1966 | Jungreis | 436/83 |
| 3,630,957 | 12/1971 | Rey et al. | 422/56 X |
| 4,263,322 | 4/1981 | vant Riet et al. | 514/575 X |
| 4,857,149 | 8/1989 | Tiedeman et al. | 162/158 |

OTHER PUBLICATIONS

Chemical Abstracts 48:901d "Photoactivation and Color Formation in Antioxidant-Treated Lard" Dugan et al.
Chemical Abstracts 53:17756c "Reaction of Molybdate and Vanadate with Phenols in Aqueous Solutions and in Concentrated Sulfuric Acid" Shaiderman et al.
Chemical Abstracts 55:2438e "Detection and Photometric Determinations of Molybdenum-(VI) with Gallic Acid" Vajda-Brown et al.
Chemical Abstracts 57:15240f "Ferrous Salts in the Assay of the Alkyl Gallates" del Pozo et al.
Buchwald et al., "The Colorimetric Determination of Molybdenium with Polyhydric Phenols" *Talanta*, 1962, 9, 631-637.
Anger et al., "Spot Tests in Inorganic Analysis" 1972, Elsevier Publishing Company-New York, pp. 269-273, 320-325 and 503-510.
Y. K. Angrawal, "Extraction and Spectrophotometric Determination of Vanadium (V) with N--Phenyl-2-Naphthohydroxamic Acid" *Anal. Chem.* 1975, 47, 940-942.
Poddar et al., "Extractive Spectophotometric Determination of V(V) Using Salicylhydroxamic Acid" *Indian J. Chem.* 1976, 14A, 546-547.
Burns et al., "The earliest Spot-Test Reaction" *Educ. Chem.* 1981, 18, 80-81.

*Primary Examiner*—Jill A. Johnston
*Assistant Examiner*—Arlen Soderquist

[57] ABSTRACT

Improved method and device for detection and semi-quantitative colorimetric determination of molybdate, ferric, and vanadate ions in aqueous solutions and coolant systems containing ethylene glycol and coolant additive. The disclosed device comprises of test strips of absorbent support carrier or water resistant film impregnated uniformly with a hydroxylamine salt and a polyhydroxy organic acid such as gallic acid or its derivatives. Molybdate ions result in an orange/brown colorataion, ferric and vanadate ions result in a grey-blue/black coloration with color intensity directly proportional to concentration of ions.

7 Claims, No Drawings

TEST DEVICE FOR DETECTION OF MOLYBDATE, VANADATE AND FERRIC IONS

BACKGROUND OF THE INVENTION

The present invention is concerned with a new, improved, and more stable colorimetric, diagnostic agent for the semi-quantitative determination of molybdate, ferric, and vanadate ions in cooling systems containing ethylene glycol or propylene glycol, or other solutions containing these ions. A further object of this invention is to provide a safe, rapid, and reliable means for testing for said ions. Another object of this invention is to produce a diagnostic test method possessing improved shelf life, useable over a wide sample temperature range (35° F. to 180° F.), useable over a wide pH range, and useable over a wide ion concentration range (10 to 4000 ppm).

Current test procedures using an absorbent support carrier (test strips) for detection of molybdate ions use dithiol or thiocyanate and tin chloride in the presence of acid for colorimetric detection. However, these methods require acid addition, use chemicals that are unpleasant in odor, are unstable, are sensitive to the presence of glycol or other interfering ions, or require several minutes for colorimetric development. It has now been found that all of the above disadvantages can be avoided by the use of this invention's stable, diagnostic test method which has a reaction time of approximately one minute.

Scientific periodicals have reported many organic hydroxy compounds that give satisfactory colorimetric reactions for determining micro-amounts of molybdenum with the use of gallic acid with cathecol, alizarin and O-hydroxycourmarins. These method require extraction to eliminate reactions with interfering ions. The formation of colorimetric complexes of molybdate ions with hydroxylamine and resorcinols, hydroxyphenols, butrylpyrogallol and gallic acid have been reported in aqueous media. However, the aqueous test solutions require mixing of reagents, pH adjustment, frequent reagent preparation due to instability, and a spectrophotometer for quantization. With the use of a suitable absorbent support or carrier, such as customarily employed for production of indicator test strips, the current invention overcomes the shortcomings of determining molybdate in aqueous media. Filter paper is most commonly employed as the absorbent support. Other absorbent support forms such as absorbent cellulose, cellulose derivatives, absorbent products such as polypropylene fiber and fiber glass laminates can likewise be used. In addition, film test strips can be made similar to film formulas identified in U.S. Pat. No. 3,630,957 or mixtures thereof but not limited to such film formulas.

DETAILED DESCRIPTION

The following examples are given for the purpose of illustrating the present invention and are not to be construed as a limitation thereof:

EXAMPLE 1

Filter paper No. 903 of Schleicher and Schuell is impregnated with the following solution:
5.0 g Propyl Gallate
5.0 g Hydroxylamine hydrochloride
100 g Methanol The impregnated paper is dried and cut into small pieces of 10×5 mm and glued to plastic strips (white PVC 0.008" thick) of 5×50 mm at the lower end thereof. Upon immersion of the test strip into a molybdate ion containing sample, the strip turns orange or brown. The molybdate ion concentration can be determined in less than one minute with the use of a standard color scale prepared from known molybdate ion concentrations. Detection sensitivity of 10 ppm and less can be observed. The color is tan or light orange at the lower concentrations and at about 4000 ppm the color is dark brown. Detection sensitivity of vanadate and ferric ions is about 5 pp.

EXAMPLE 2

Filter paper 12S of Schleicher and Schuell is impregnated with the following solution:
To 5.0 g Hydroxylamine sulfate dissolved in 40 g distilled water is added 4.0 g 2,3,4 Trihydroxylbenzoic Acid dissolved in 60 g Ethanol.

Analogous to Example 1, test strips are prepared. Reactivity, color development, and sensitivity to the ions as in Example 1 are found.

EXAMPLE 3

A test strip according to example 1 wherein said impregnation is with the following solution:
4.0 g 3,4,5 Trihydroxybenzoic Acid (Gallic Acid)
5.0 g Hydroxylamine hydrochloride
0.8 g Tris Amino (Tris(hydroxymethyl)aminomethane)
100 g Methanol

EXAMPLE 4

A reagent film for the detection of molybdate, vanadate, or ferric ions in solution was prepared as follows:
100.0 g Polyvinyl propionate dispersion
2.0 g Hydroxylamine hydrochloride
1.7 g 3,4,5 Trihydroxybenzoic Acid
0.2 Tris Amino The above was applied in a 8 mil thick layer onto a white polyvinyl chloride sheet and then air dried with warm air. This formed a water-insoluble film which provides a graduated orange or ochre color to brown (low to high levels of molybdate) on reaction with molybdate ions in solution. The color produced is readily seen against the white background of the PVC.

EXAMPLE 5

A test strip according to example 4 wherein said film is layered on transparent PVC film. The transparent film after reaction with molybdate ions can now be quantitated by spectrophotometric transmission analysis at the appropriate wavelength. Optical density of the strip increases proportionally to increasing concentrations of molybdate ions.

In addition to the above reagent combinations, that any of a variety of hydroxylamine salts, but not limited to these salts, such as hydrochloride, sulfate, and phosphate may be used; in addition, hydroxylamine-0-sulfonic acid, 0-ethyl hydroxylamine hydrochloride, N-methyl hydroxylamine hydrochloride, methoxylamine hydrochloride or any salts thereof or mixtures of any of the above salts may be used with any of a variety of polyhydroxy organic reagents or mixtures thereof. Examples of polyhydroxy organic reagents include 2, 3, 4 Trihydroxybenzoic Acid; 3, 4, 5 Trihydroxybenzoic Acid (Gallate); Methyl 3, 4, 5 Trihydroxybenzoate; Propyl 3, 4, 5 Trihydroxybenzoate; Lauryl 3, 4, 5 Trihydroxybenzoate; and a variety of polyhydroxy organics of similar structure can be used thereof or in combination.

The pH of the sample for colorimetric reactivity is 1.0 up to 9.5. When measurement for a specific ion in the presence of the other reacting ions is desired, then the use of masking agents should be used. For example, if molybdate is to be measured in the presence of ferric ions, then the ferric ion interference can be masked by the addition of tartaric acid, tetraacetic acid, or another masking agent to the solution to be tested.

What is claimed:

1. A diagnostic element for semi-quantitative detection of molybdate, ferric, or vanadate ions in solution comprising: a bibulous, fibrous, carrier member uniformly impregnated with a reagent consisting essentially of a trihydroxybenzoic acid or trihydroxybenzoic acid ester and a hydroxylamine salt.

2. The diagnostic element as in claim 1 wherein the trihydroxybenzoic acid or trihydroxybenzoic acid ester is selected from the group consisting of 2,3,4-trihydroxybenzoic acid, 3,4,5-trihydroxybenzoic acid, methyl gallate, propyl gallate, lauryl gallate, and mixtures thereof and the hydroxylamine salt is selected from the group consisting of hydroxylamine hydrochloride, hydroxylamine sulfate, hydroxylamine phosphate, hydroxylamine-O-sulfonic acid, O-ethyl hydroxylamine hydrochloride, N-methyl hydroxylamine hydrochloride, methoxylamine hydrochloride, and mixtures thereof.

3. The diagnostic element as in claim 2 wherein the trihydroxybenzoic acid or trihydroxybenzoic acid ester is propyl gallate and the hydroxylamine salt is hydroxylamine hydrochloride.

4. The diagnostic element as in claim 2 wherein the trihydroxybenzoic acid or trihydroxybenzoic acid eater is 2,3,4-trihydroxybenzoic acid and the hydroxylamine salt is hydroxylamine sulfate.

5. A diagnostic element for semi-quantitative detection of molybdate, ferric, or vanadate ions in solution comprising: a bibulous, fibrous, carrier member uniformly impregnated with a reagent consisting essentially of 3,4,5-trihydroxybenzoic acid, hydroxylamine hydrochloride, and tris(hydroxymethyl)aminomethane buffer.

6. A diagnostic element for semi-quantitative detection of molybdate, ferric, or vanadate ions in solution comprising: a homogeneous water-resistant film formed from a mixture of aqueous dispersions of a natural or synthetic polymer and a reagent consisting essentially of 3,4,5-trihydroxybenzoic acid, hydroxylamine hydrochloride, and tris(hydroxymethyl)aminomethane buffer.

7. The diagnostic element as in claim 6 wherein the homogeneous water-resistant film is layered uniformly on a rigid polyvinyl chloride film allowing analysis in a spectrophotometer.

* * * * *